United States Patent [19]
Wach et al.

[11] Patent Number: 5,911,017
[45] Date of Patent: Jun. 8, 1999

[54] FIBER OPTIC INTERFACE FOR LASER SPECTROSCOPIC RAMAN PROBES

[75] Inventors: Michael Leonard Wach, Byron, Ga.; Gregory J. Gervasio, Wildwood, Mo.

[73] Assignee: Visionex, Inc., Warner Robins, Ga.

[21] Appl. No.: 08/901,603

[22] Filed: Jul. 28, 1997

Related U.S. Application Data

[60] Provisional application No. 60/023,310, Jul. 31, 1996.

[51] Int. Cl.$^6$ ....................................... G02B 6/00
[52] U.S. Cl. ............................ 385/12; 385/133; 385/121; 385/31
[58] Field of Search ................................. 385/12, 31, 32, 385/115, 116, 117, 118, 119, 120, 121, 133

[56] References Cited

U.S. PATENT DOCUMENTS

| | | | |
|---|---|---|---|
| 3,806,256 | 4/1974 | Ishak ........................................ | 356/186 |
| 4,573,761 | 3/1986 | McLachlan et al. ................. | 350/96.24 |
| 4,707,134 | 11/1987 | McLachlan et al. ..................... | 356/342 |
| 4,812,003 | 3/1989 | Dambach et al. .................... | 350/96.18 |
| 4,816,670 | 3/1989 | Kitamura et al. ........................ | 250/227 |
| 4,914,284 | 4/1990 | Halldorsson et al. ................... | 250/206 |
| 5,112,127 | 5/1992 | Carrabba et al. ......................... | 356/301 |
| 5,166,756 | 11/1992 | McGee et al. ........................... | 356/446 |
| 5,253,312 | 10/1993 | Payne et al. .............................. | 385/31 |
| 5,402,508 | 3/1995 | O'Rourke et al. ........................ | 385/31 |
| 5,652,810 | 7/1997 | Tipton et al. .............................. | 385/12 |
| 5,764,840 | 6/1998 | Wach ....................................... | 385/123 |

FOREIGN PATENT DOCUMENTS

| 0286419 | 4/1988 | European Pat. Off. . |

OTHER PUBLICATIONS

Boiarski A., "Fiber Optic Particle Concentration Sensor", SPIE vol. 566 *Fiber Optic and Laser Sensors III*, 1985, pp. 122–125.

Krohn D., "Intensity Modulated Fiber Optic Sensors Overview", SPIE vol. 718 *Fiber Optic and Laser Sensors IV*, 1986, pp. 2–11.

*Primary Examiner*—Phan Palmer
*Attorney, Agent, or Firm*—Jones & askew, LLP

[57] ABSTRACT

A fiber optic interface for laser spectroscopic Raman probes incorporating a housing with a window enclosure. The fiber optic interface minimizes stray light interference from window back reflections and provides high photonic efficiency through refractive manipulation of emission and reception fields. The illumination fiber is surrounded by collection fibers. The fiber bundle formed by the illumination fiber and the collection fibers is formed into a conical shape, which creates a refractive surface on the illumination fiber and each of the collection fibers. The refraction at the end faces steers the illumination and collection patterns toward the axis of the illumination fiber. This results in the reflected portion of the illumination light being reflected toward the illumination fiber, and in the collection pattern being coincident with the illumination pattern.

19 Claims, 3 Drawing Sheets

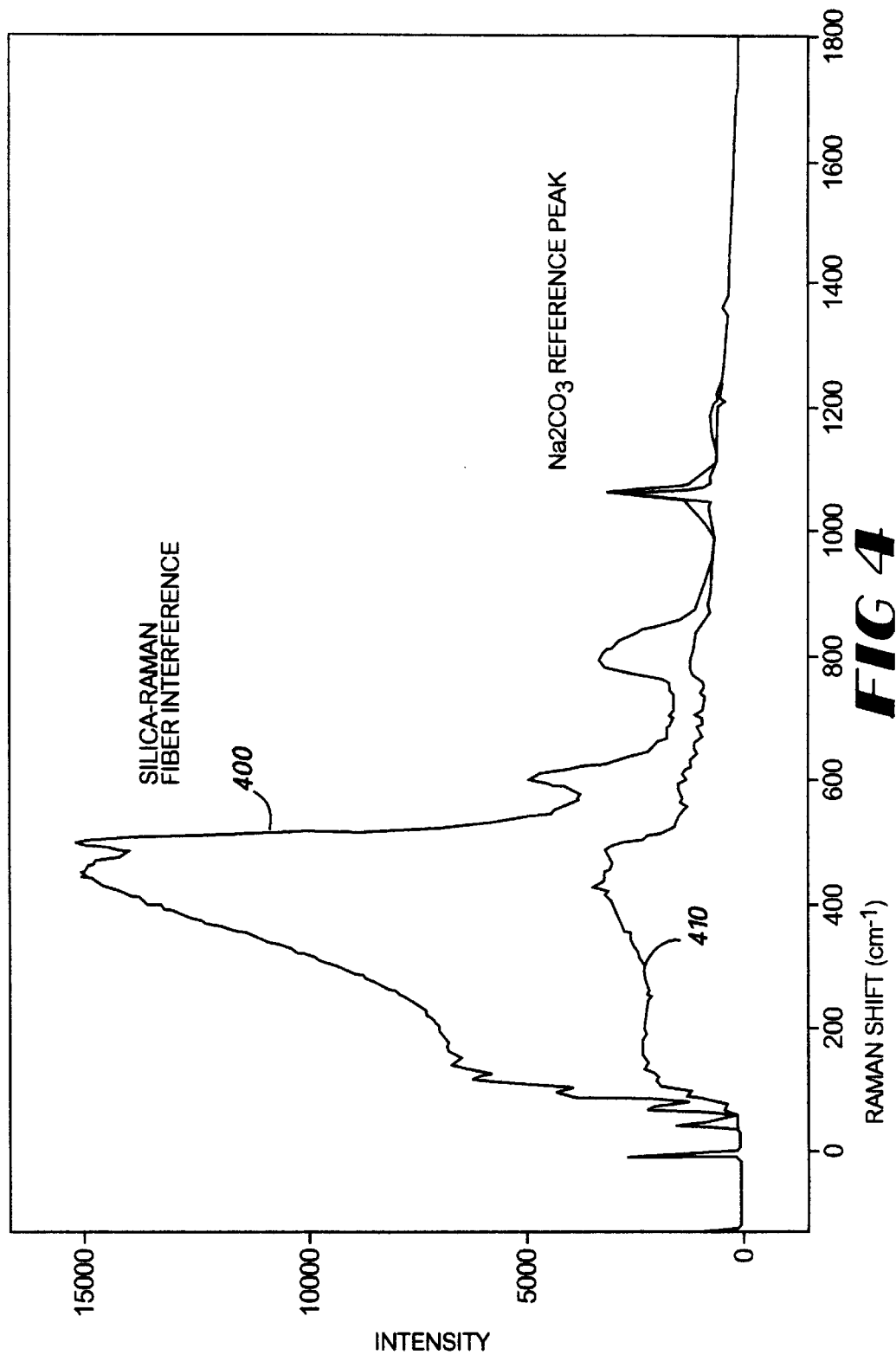

FIBER OPTIC INTERFACE FOR LASER SPECTROSCOPIC RAMAN PROBES

STATEMENT REGARDING RELATED APPLICATIONS

This application claims the benefit of U.S. Provisional Application No. 60/023,310, entitled "Fiber Optic Interface for Laser Spectroscopic Raman Probes," filed Jul. 31, 1996.

TECHNICAL FIELD

The present invention is related to fiber optic probes for Raman spectroscopy. More particularly, it relates to improved fiber optic interfaces and their incorporation into probes for enhanced photonic efficiency and improved rejection of unwanted signals.

BACKGROUND OF THE INVENTION

Raman spectroscopy is an analytical technique that has a tremendous variety of potential uses. Among other desirable characteristics, Raman spectroscopy is compatible with aqueous media and does not typically require sample preparation. The technique is particularly attractive due to its suitability for remote analysis via optical fiber. By employing optical fibers as light conduits, the light source and light detector can be physically separated from the sample. This remote attribute is particularly valuable in process control and especially in sensing and analysis involving harsh chemicals in hostile environments.

In a typical configuration for fiber-optic-based Raman analysis, one or more illumination fibers deliver light from a source to the sample. The light source is typically a laser, and this type of analysis is often referred to as a branch of fiber-optic-based laser spectroscopy. Upon interaction with the sample, the laser light is scattered into distinct wavelengths that differ from the laser wavelength. One or more collection fibers receive the scattered light from the sample and transmit it to a detector. The characteristics of the source light are compared to that of the received light. Two characteristics are particularly important. The wavelength separations between the laser light and the bands of scattered light are specific to the chemicals within the sample. The spectral intensity of the scattered light is a function of the sample's chemical concentration.

The Raman scattering effect is extremely weak. Only a small fraction of the excitation light is Raman scattered. Because the signals are weak, the probe's delivery of light to and collection of light from the sample must be highly efficient. And, the introduction of extraneous signals severely corrupts the measurement quality.

When sampling fluid media, the sample to be analyzed is often flowing within a pipeline or is turbulent in a reactor vessel. The medium under inspection is often dark or exhibits other aspects that complicate the measurement.

In process control environments, the conditions are often so hostile as to necessitate physical and chemical isolation of the probe's optical fibers from the surrounding environment. To accomplish such isolation, a probe may incorporate a window behind which its fibers are positioned. The incorporation of a window into a probe introduces a significant engineering problem. As emitted illumination light passes through the window and into the sample, a portion of this light is back reflected by the window's inner and outer surfaces. In the prior art, this undesired back reflected light is inadvertently introduced into the collection fibers along with the desired Raman scattered light. The back reflected light corrupts the quality of the analysis. Light inadvertently introduced into a photonic instrument is often referred to as stray light.

The issue of stray light in fiber optic probes for Raman spectroscopy is complicated by another factor. As laser light propagates through the fiber from the source to the sample, the light interacts with the fiber core and is scattered. Fiber scattering effects may include fiber fluorescence, Raman scattering, and other interference. This fiber-scattered light will be referred to as silica-Raman light, but is not exclusive to silica fibers or to the Raman effect. The longer the optical fiber, the more intense the silica-Raman light. Thus, the light that is back reflected off the probe window contains silica-Raman light in addition to the primary laser light. This silica-Raman light is particularly troublesome to the measurement as it is spread over broad wavelengths. Once mixed with the desired Raman light from the sample and introduced into the collection fiber, the desired light cannot be easily isolated from the silica-Raman light. The problem is further complicated because back reflected laser light, which is inadvertently received by the collection fibers, also generates silica-Raman light as it propagates from the probe to the detector.

The prior art includes a variety of attempts to address the problems discussed above.

U.S. Pat. No. 5,166,756 to McGee et al. describes a probe for analyzing powders. In this probe, a multiplicity of illumination and collection fibers are arranged behind a sapphire rod. The rod's end face is inclined relative to the optical fibers' end faces. In accordance with the patent's teaching, back reflections from the rod's outer surface are angularly oriented outside of the collection fibers' reception capabilities. In this manner, the subject can be analyzed with reduced interference from window reflection.

The probe described in McGee et al. suffers from several drawbacks. The window's thickness removes the fibers a significant distance from the sample, which results in decreased efficiency. The overlap between the illumination zone and the collection fibers' field of view is not precisely controlled. This also contributes to poor efficiency and requires the use of finely stranded fiber optic bundles, which also suffer from many drawbacks. The probe's optical characteristics are dependent on the position of the illumination and collection fibers relative to the window's outer surface and to one another. Maintaining repeatability of these factors is difficult in fabricating the probe. Therefore, probe-to-probe performance repeatability, particularly as it relates to broad band intensity, suffers.

Similar problems plague related methodologies that angularly orient various aspects of a window such that the window's planar surfaces are not perpendicular to the fiber's longitudinal axis. For example, U.S. Pat. No. 4,573,761 to McLachlan et al. describes a probe in which the optical axis of an illumination fiber and the axes of multiple collection fibers are directed into intersection by bending the collection fibers near their ends. From their positions behind a window, the collection fibers receive back reflections from the window. These reflections greatly reduce measurement quality.

U.S. Pat. No. 5,402,508 to O'Rourke et al. describes a probe that employs shaped end faces on parallel fibers to improve optical efficiency. Refraction at the fiber's end face bends the fibers' illumination and viewing fields toward overlapping regions. Although this concept appeared to be promising, it suffers from several limitations.

Although O'Rourke et al. teach that reflections from a window's outer surface are not troublesome for deployment in liquids, the opposite is often the case. Windows fabricated from strong, chemically resistant materials, such as sapphire and diamond, have refractive indices that are much higher than most solutions. For example, sapphire's refractive index is approximately 1.77, while water's refractive index is about 1.33. This refractive index differential results in the reflection of light exiting the window. Lower refractive index window materials such as silica can be employed. However, because these materials are typically much weaker and less chemically resistant, their usage requires a thick window. The increased window thickness results in increased back reflection and decreased collection efficiency.

A sample's refractive index can vary depending on many factors, including temperature and composition. The refractive index often changes independently of the parameter that the analysis seeks to isolate. Therefore, the stray light cannot be easily removed by compensation.

In gaseous media such as air, the problem is particularly acute. Although usage of thin windows minimizes the collection of back reflections arising from a window's outer surface, thin window attachment to the probe housing is difficult and the resulting assembly is mechanically weak.

The preferred embodiment described by O'Rourke et al. depicts the illumination and collection fibers as being separated by a gap. This type of separation can be utilized to minimize the collection of window-based back reflection. However, the separation between illumination and collection fibers results in poor photonic efficiency.

In another prior art approach, probes were formed by encircling a flat-faced illumination fiber with a ring of flat-faced collection fibers. The resulting fiber optic bundle was then positioned behind a window. The illumination fiber emits light through the window and into a sample. The collection fibers receive light scattered by the sample. When the illumination and collection fibers are flat, the optical axes of the emission and reception patterns do not intersect and the probe is inefficient. In addition, the probe suffers from stray light arising from back reflection of illumination light from the window's outer surface.

Improved performance was accomplished by shaping the end of the group of collection fibers, while leaving the center illumination fiber flat. In particular, the probe's center fiber end face remains flat, and the surrounding fibers' end faces are angled and formed on a taper. This results in a taper between the bundle's outer cylindrical surface and the center fiber's flat end face. The refractive effect of the shaped end faces causes the collective field of view of the collection fibers to converge on the optical axis of the illumination fiber. The overlap between the illumination fiber's emission zone and the collection fibers' reception zone, which occurs in the sampled medium, is established fairly close to the probe end face and, when compared to flat-faced probes, results in increased photonic efficiency, especially in dark, absorbing media. However, even with all of its desirable characteristics, this type of probe is prone to stray light from back reflections of emitted light off the window.

A variety of filtering techniques have also been employed in various attempts to overcome the described problems. However, their usage involves many engineering challenges and application-related limitations.

Therefore, there is a need in the art for a probe that minimizes stray light resulting from window reflections while concurrently providing controlled overlap between the illumination fibers' emission fields and the collection fibers' reception fields.

SUMMARY OF THE INVENTION

The present invention satisfies the above-described need by providing a simple probe that reduces stray light arising from window back reflections and also provides efficient coupling in various media, including dark, absorbing media and those exhibiting interference from Rayleigh-scattering. A fiber optic interface according to the invention improves rejection of stray light for window-based probes and provides efficient transfer of light into and from a sample.

Generally described, the interface is created by adapting a grouping, or bundle, of optical fibers positioned behind a window. The bundle includes a plurality of collection fibers that surround an illumination fiber. The illumination fiber emits light into a sample and the plurality of collection fibers receive light from the sample. The entire end face of the bundle is formed into a cone with the vertex of the cone positioned at the center fiber's center. The cone shape imparts a refractive surface on each of the fibers. This has a refractive effect on the light emitted from the illumination fiber and on the received light incident on the collection fibers. The refractive effect imparts a converging aspect to the emitted light such that window reflections of emitted light are directed back into the illumination fiber. In this manner, the quantity of window reflections received by the collection fibers are minimized. Each collection fiber's field of view is directed inward by refraction so that each field of view axis intersects with the optical axis of the illumination fiber's emission pattern.

Generally described, the present invention provides a fiber optic probe assembly. The assembly includes an illumination fiber for transmitting light from a source to a sample and a plurality of collection fibers centered about and parallel to the illumination fiber. A bonding agent holds the illumination fiber and the collection fibers together to form a fiber bundle, which has a conical shape. The conical shape forms a refractive surface on the illumination fiber and on each of the collection fibers. A housing encloses the conical shaped fiber bundle. A window is mounted in the end of the housing and in contact with the vertex of the conical shaped fiber bundle. The light from the illumination fiber is transmitted through the window into the sample, and the collected light is transmitted from the sample to the collection fibers through the window.

More particularly described, the present invention includes a medium that fills the space between the fiber bundle and the window. The medium has a refractive index that is lower than that of the illumination and collection fibers. Refraction at the refractive surface of the illumination fiber steers the light emitted by the illumination fiber toward the axis of the illumination fiber and away from the collection fibers. Refraction at the refractive surface of the collection fibers steers the collection zone toward the axis of the illumination fiber. This steering effect may be used to cause the illumination zone and collection zone to overlap at a point external to the window.

In another aspect, the present invention provides a fiber optic probe interface for Raman analysis. The probe interface includes a cylindrical housing with an opening at an end, and a window mounted in the opening. A bundle of optical fibers is mounted in the housing. The bundle includes an illumination fiber and a plurality of collection fibers centered about the illumination fiber. The bundle has a conical shape, which provides a shaped end face on the illumination fiber and on each of the collection fibers. The vertex of the conical shaped bundle is adjacent the window. A medium fills the space between the bundle and the window. The medium has a refractive index lower than that of the illumination and collection fibers.

More particularly described, the refractive effect on the light emitted from the shaped end face of the illumination fiber is essentially symmetrical about the illumination fiber's center axis. And, the magnitude of the refractive effect on the light emitted from the shaped end face of the illumination fiber is essentially independent of radial offset from the illumination fiber's center axis.

The various aspects of the present invention may be more clearly understood and appreciated from a review of the following detailed description of the disclosed embodiments and by reference to the appended drawings and claims.

BRIEF DESCRIPTION OF THE DRAWINGS

FIG. 4 is a graph illustrating the performance increase of a probe that incorporates the present invention.

DETAILED DESCRIPTION

Figure 1:
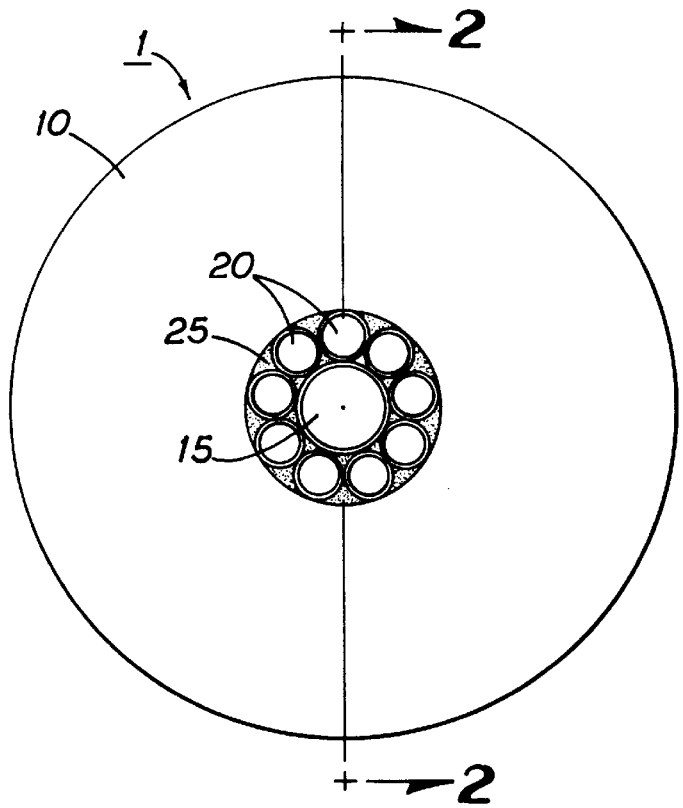
FIG. 1 is a plan view of a fiber optic probe end face that employs an embodiment of the present invention.

The present invention is directed to an improved fiber optic interface. In an exemplary embodiment, a fiber optic probe includes a single illumination fiber that is surrounded by a plurality of collection fibers. The fiber bundle that is formed by the illumination and collection fibers is formed into the shape of a cone. Refraction at the shaped end faces causes the illumination and collection zones to overlap and also causes most of the illumination light that is reflected off the probe's window to be reflected back toward the illumination fiber instead of toward the collection fibers.

The advantages of the present invention may best be understood by comparing an exemplary embodiment of the present invention to prior art devices. As mentioned above, some prior art probes were formed by encircling a flat-faced illumination fiber with a ring of flat-faced collection fibers. The resulting fiber optic bundle was then positioned behind a window. When the illumination and collection fibers are flat, the optical axes of the emission and reception patterns do not intersect and the probe is inefficient. In addition, the probe suffers from stray light arising from back reflection of illumination light from the window's outer surface.

In an improved prior art approach, a flat-faced illumination fiber is surrounded by a group of collection fibers with tapered end faces. The refractive effect of the shaped end faces directs each collection fiber's field of view such that each collection fiber's individual optical axis intersects the optical axis of the illumination fiber at some distance into the sample medium. This induces overlap between the illumination fiber's emission zone and the collection fibers' reception zone. This overlap is established fairly close to the probe end face and, when compared to flat-faced probes, results in increased photonic efficiency, especially in dark, absorbing media. Even with all of its desirable characteristics, this probe is prone to stray light from back reflections of emitted light off the window.

Referring now to the drawings, in which like numerals represent like elements throughout the several figures, aspects of the present invention will be described.

Figure 2:
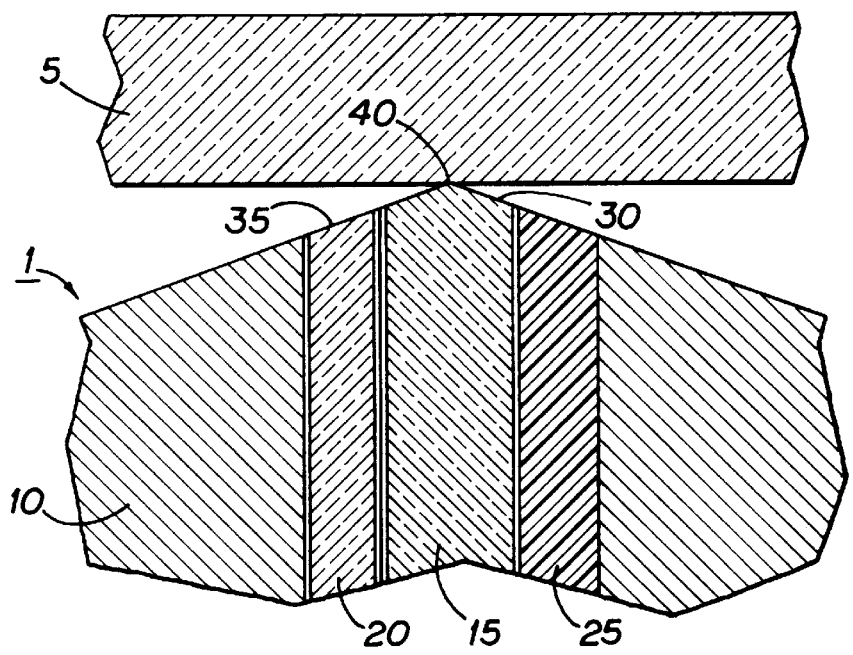
FIG. 2 is a cross-sectional view of the fiber optic probe depicted in FIG. 1 taken along the line 2—2.

The present invention provides an improved fiber optic interface that overcomes the limitations associated with the previously described probes. An exemplary embodiment of the present invention is illustrated in FIGS. 1 and 2, which are ortho-normal views of the same probe. FIG. 1 is an overhead view. FIG. 2 is a cross-sectional taken along the line 2—2 of FIG. 1. For clarity, the window is not depicted in FIG. 1.

In an exemplary embodiment, a fiber optic probe 1 in accordance with the present invention includes a bundle of optical fibers. The bundle includes a center illumination fiber 15 and a plurality of collection fibers 20, which surround the illumination fiber 15. The bundle is positioned behind a window 5 formed of sapphire. Although the thickness of the window 5 can range between approximately 0.005–0.080 inches, the preferred thickness is approximately 0.020 inches.

The end face surface of the center illumination fiber 15 is formed into a shape defined by the revolution of a right triangle about one of the triangle's legs—geometrically a cone. The cone-shaped end face's point 40, or vertex, is located essentially at the center of the center illumination fiber 15. The end faces 35 of the surrounding collection fibers 20 are tapered on an angle that is an outward extension of the center fiber's end face 30. The bundle is bound by bonding agent 25 and mounted in a cylindrical housing 10. Cross-talk between the bundle's fibers may be inhibited by a variety of methods, such as applying carbon-loaded epoxy to bind the fibers to one another and to the housing's side walls. The tip 40 of the center illumination fiber 15 is in contact with the inner surface of the window 5.

As light is emitted from the end face 30 of the illumination fiber 15, it is refracted. The refraction occurs as a result of the conical shape of the end face 30 and its differential refractive index interface. The refractive index differential is created by the relatively high refractive index of the fiber core and the relatively low index of the medium that fills the space between the fiber end face 30 and the window 5. The refraction imparts a convergence aspect to the emitted light. Window back reflections from the emitted converging rays are directed generally inward towards the center illumination fiber's center axis and back into the center illumination fiber 15. Hence, unwanted collection of window back reflected light by the collection fibers is minimized and stray light interference is reduced.

The conical end face 30 is preferably formed with a 20° angle between the cone's side and the inner surface of the window 5. This angle is identical to the inclination angle, which refers to the angle between the cone base and the cone side. In testing, a 20° angle has proven excellent to minimize stay light arising from back reflections of laser and silica-Raman light in the illustrated probe 1, which incorporates silica core/silica clad fibers with a 0.22 numerical aperture. The general range for this angle is approximately 10 to 35 degrees. Lesser angles have been shown to provide decreased performance, which is apparently due to the reduction in imparted refraction. Those skilled in the art will understand that the angle may need to be changed for changes in the fiber and fluid refraction index.

The inclination angle can be such that refraction directs a first portion of the emitted light into convergence while a second portion of the emitted light diverges under the cone's refractive effects. Division into convergence or divergence is due to the random angular orientation of light propagating within the illumination fiber. The inclination angle can also be formed such that essentially none of the illumination represented in the fully filled, normal modes of the illumination fiber diverges. The inclination angle also can be formed such that essentially all of the illumination represented in the fully filled, normal modes of the illumination fibers converges. For one embodiment, the inclination angle can be between approximately 5 and 25 degrees. For another embodiment, the inclination angle is approximately between 20 and 35 degrees.

The thickness of the window 5 can be within a range of approximately 0.005–0.080 inches, preferably 0.020 inches, and the window can be formed of transparent optical material, such as quartz, glass, or sapphire. For the preferred embodiment, the window comprises sapphire. The illumination fiber can have a core diameter of approximately 50–600 microns, preferably about 400 microns. The diameters of the collection fibers can be approximately 50–600 microns and are independently selected from the diameter of the illumination fiber. Each collection fiber has a preferred diameter of approximately 200 microns. The illumination fiber can propagate laser light. The illumination fiber also can generate and propagate extraneous, unwanted light, such as that generally known as silica-Raman and fiber fluorescence.

An important quality of the refraction that occurs at the center illumination fiber's end face 30 is that its magnitude is essentially independent of the radial offset from the end face point 40, which is located that the center of the illumination fiber 15. Thus, rays that emerge from the fiber's end face 30 near the end face point 40 are refracted to an inward orientation essentially the same as rays that emerge from the fiber's end face 30 near its outer rim. And, the refraction is symmetrical about the center axis of the illumination fiber 15. These properties, which account for the probe's performance, cannot be achieved with end faces such as angled planar, ball, radiused, etc. The result of the invention is the projection of intense light immediately outside of the outer surface of the window 5.

The collection fibers 20 are formed with refracting end faces 35 that are outward extensions of the center illumination fiber's end face conical form. The effect on the collection fiber's field of view is consistent with that previously described for probes that employ a flat-faced illumination center fiber surrounded by tapered collection fibers.

As described earlier, the refractive effects imparted on light emitted from the center illumination fiber has been shown to be essentially independent of radial offset of the emission from the fiber's center point. The refractive effect imparted on received light by the collection fiber's shaped end faces 35 is likewise symmetrical. Thus, the refraction imposed on the illumination fiber's emission field is essentially the same as the refraction imposed on the collection reception field. This property imposes an overlap of the emission and reception fields that extends far beyond the window's outer surface.

In the illustration of FIGS. 1 and 2, the probe is depicted as having nine surrounding collection fibers 20, which are 200-micron core diameter fibers. The depicted probe includes one center illumination fiber 15, which is a 400-micron core diameter fiber. The core-diameter-to-cladding-diameter ratio is 1:1.1. The 2:1 center-fiber-diameter-to-surrounding-fiber-diameter ratio provides good photonic coupling efficiency by minimizing the separation between illumination and collection end face areas. It also facilitates efficient coupling into detectors that have slit input geometry. It will be appreciated that other fiber sizes can be used.

Probes incorporating fiber optic interfaces of the present invention can be fabricated with modified fiber optic processing equipment. The probe's fiber optic bundle is held by a collet, chuck, or similar device that allows it to spin while maintaining an angular orientation. The bundle's axis of rotation is set so that the bundle spins about the cone's axis. The bundle is set so as to contact an abrasive rotating disk. The angle between the abrasive disk defines the end face cone angle. The abrasive grit of the rotating disk is decreased in grinding passes in order to achieve a fine optical polish.

The bundle is preferentially positioned in a sealed chamber incorporating a thin transparent window. The window may be attached and sealed to a metal sleeve by brazing. The window-metal sleeve assembly may then be attached and sealed to the probe housing by many methods. For the present invention to be effective, the center fiber's cone end tip should remain in intimate contact with the window's inner surface.

Figure 3:
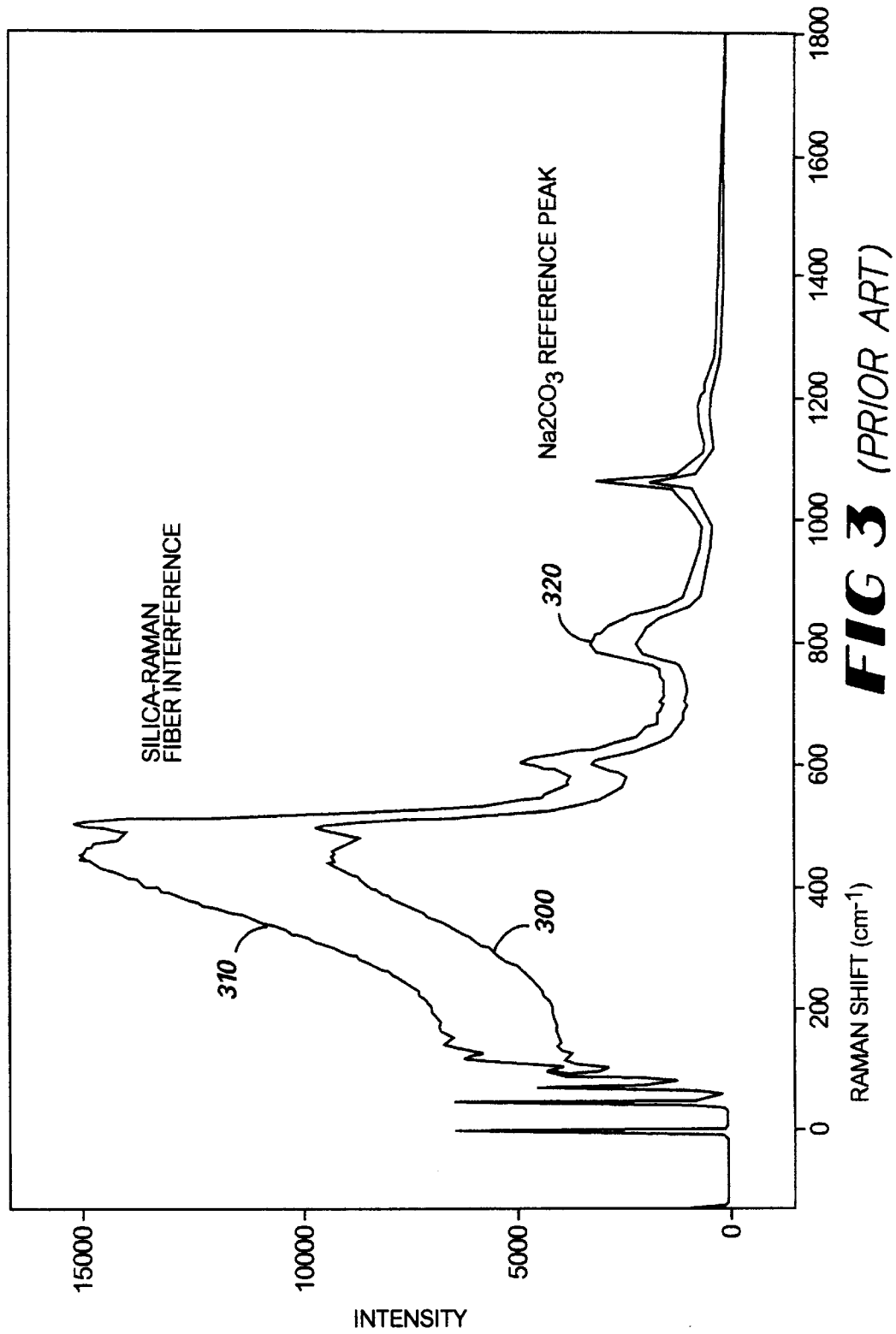
FIG. 3 is a graph illustrating the performance of two prior art probes in which increased collection of desired scattered light from the sample results in worsened stray light performance.

FIG. 3 and FIG. 4 illustrate test results for windowed probes conducted in an aqueous test solution comprising water and dissolved $Na_2CO_3$. The broad spectral structures, essentially between 0 $cm^{-1}$, and 1000 $cm^{-1}$, are unwanted silica-Raman signals resulting primarily from back reflected light off the window. Lower spectral intensity in this wavelength region corresponds to improved probe performance. The silica-Raman intensity peaks at 486 $cm^{-1}$. The spectra also exhibits a peak at 1065 $cm^{-1}$. This peak is due to the $Na_2CO_3$ additive. Its intensity, or height, is a measure of the probe's ability to collect the desired Raman-scattered light from the sample. Because the silica-Raman artifact extends into the 1065 $cm^{-1}$, region, the height of the peak must be evaluated carefully. The peak height is measured between the peak's highest point and the top of the underlying silica-Raman structure, which appears as a broad peak.

FIG. 3 presents test results that compare the performance of two prior art probes. The lower spectrum 300 is produced by a prior art probe incorporating a flat-faced center illumination fiber surrounded by flat-faced collection fibers. The upper spectrum 310 is produced by a more advanced prior art probe that incorporates a flat-faced center illumination fiber surrounded by tapered collection fibers. The collection fibers' end faces are tapered such that a 20° angle is formed between the end face surface and the window's inner surface. The probe with the tapered collection fibers exhibits increased performance in terms of collection of the $Na_2CO_3$ desired signal as is evident by its higher peak 320 at 1065 $cm^{-1}$. However, the probe with the tapered collection fibers exhibits markedly decreased performance in terms of stray light as is evident by its larger silica-Raman artifacts.

FIG. 4 presents test results comparing the performance of a probe constructed in accordance with an embodiment of the present invention and a prior art probe. The upper spectrum 400 is produced by a prior art probe that incorporates a flat-faced center illumination fiber surrounded by tapered collection fibers. The collection fibers' end faces are tapered such that a 20° angle is formed between the end face surface and the window's inner surface. The lower spectrum 410 is produced by a probe that incorporates fiber optic interface advancements of the present invention. In this new probe, the entire bundle end face, including both center illumination and surrounding collection fibers, is formed in accordance with the described methods of the present invention and has a 20° cone-shaped end face (the 20° angle is measured in accordance with the described convention). Both probes exhibit essentially equal performance in terms of collection of the $Na_2CO_3$ desired signal as is evident by the approximately equal peak heights at 1065 $cm^{-1}$. However, the probe incorporating the present invention exhibits markedly increased performance in terms of stray light rejection. The stray light rejection is evident by the remarkably lower silica-Raman light artifacts.

From the foregoing description, it will be appreciated that the present invention provides an improved fiber optic interface for use in a Raman-type probe. In an exemplary probe, a center illumination fiber is surrounded by a plurality of parallel collection fibers. The fiber bundles that is formed by the illumination and collection fibers is formed into the shape of a cone. Refraction at the fibers' end faces results in improved performance by causing the illumination and collection zones to overlap and by directed reflected illumination light back into the illumination fiber and away from the collection fibers.

Although the invention was described in the context of a probe in which the center fiber is utilized in an illumination capacity, the present invention offers benefits for other light-scattering spectroscopic techniques such as fluorescence and diffuse reflectance. Furthermore, the techniques offer benefits to probes in which the center fiber is utilized in a collection capacity and the surrounding fibers are utilized in an illumination capacity.

The present invention has been described in relation to particular embodiments which are intended in all respects to be illustrative rather than restrictive. Alternative embodiments will become apparent to those skilled in the art to which the present invention pertains without departing from its spirit and scope. Accordingly, the scope of the present invention is defined by the appended claims rather than the foregoing description.

What is claimed is:

1. A fiber optic probe assembly comprising:
    an illumination fiber for transmitting light from a source to a sample;
    a plurality of collection fibers, centered about and parallel to the illumination fiber, for receiving collected light;
    a bonding agent for holding the illumination fiber and the collection fibers together to form a fiber bundle, the fiber bundle having a conical shape forming a refractive surface on the illumination fiber and each of the collection fibers;
    a housing for enclosing the conical shaped fiber bundle; and
    a window mounted in the end of the housing and in contact with a vertex of the conical shaped fiber bundle, the light from the illumination fiber being transmitted through the window into the sample, and the collected light being transmitted from the sample to the collection fibers through the window;
    wherein the vertex is located on a longitudinal axis of the illumination fiber.

2. The fiber optic probe assembly of claim 1, wherein the bonding agent includes a cross-talk inhibitor.

3. The fiber optic probe assembly of claim 2, wherein the bonding agent comprises an epoxy and the cross-talk inhibitor comprises carbon black.

4. The fiber optic probe assembly of claim 1, wherein refraction at the refractive surface of the collection fibers steers a collection zone toward the axis of the illumination fiber.

5. The fiber optic probe assembly of claim 1, wherein refraction at the refractive surface of the illumination fiber and the collection fibers causes an illumination zone and a collection zone to overlap at a point external to the window.

6. The fiber optic probe assembly of claim 1, further comprising a medium filling the space between the fiber bundle and the window, the medium having a refractive index lower than that of the illumination and collection fibers.

7. The fiber optic probe assembly of claim 1, wherein refraction at the refractive surface of the illumination fiber steers the light emitted by the illumination fiber toward the axis of the illumination fiber and away from the collection fibers.

8. A fiber optic probe interface for Raman analysis, comprising:
    a housing having an opening at an end;
    a window mounted in the opening at the end, the window sealing the end of the housing;
    a bundle of optical fibers mounted in the housing, the bundle including an illumination fiber for transmitting light and a plurality of collection fibers, centered about the illumination fiber, for receiving collected light, the bundle having a conical shape providing a shaped end face on the illumination fiber and on each of the collection fibers, the vertex of the conical shaped bundle being proximate to the window and located on a longitudinal axis of the illumination fiber; and
    a medium filling the space between the bundle and the window, the medium having a refractive index lower than that of the illumination and collection fibers.

9. The fiber optic probe interface of claim 8, wherein the shaped end faces of the collection fibers cause refraction on received light incident on the shaped end faces of the collection fibers.

10. The fiber optic probe interface of claim 9, wherein the optical axis of the illumination fiber's emission pattern intersects with the optical axes of the collections fibers' fields of view.

11. The fiber optic probe interface of claim 9, wherein the collective optical axis of the collection fibers' field of view is concurrent with the optical axis of the illumination fiber's emission pattern.

12. The fiber optic probe interface of claim 8, further comprising a bonding agent for holding the illumination and collection fibers in the bundle.

13. The fiber optic probe interface of claim 8, further comprising a cross-talk inhibitor between the illumination fiber and the collection fibers.

14. The fiber optic probe interface of claim 8, wherein the refractive effect on light emitted from the shaped end face of the illumination fiber is essentially symmetrical about the illumination fiber's center axis.

15. The fiber optic probe interface of claim 8, wherein the refractive effect on the magnitude of the light emitted from the shaped end face of the illumination fiber is essentially independent of radial offset from the illumination fiber's center axis.

16. The fiber optic probe interface of claim 8, wherein the optical axis of an illumination light pattern is essentially concurrent with the outward projection of the illumination fiber's physical axis.

17. The fiber optic probe interface of claim 8, wherein refraction at the shaped end face of the illumination fiber steers the light emitted by the illumination fiber toward the axis of the illumination fiber and away from the collection fibers.

18. The fiber optic probe interface of claim 8, wherein refraction at the shaped end faces of the collection fibers steers a collection zone toward the center of the illumination fiber.

19. The fiber optic probe interface of claim 8, wherein refraction at refractive surfaces of the illumination fiber and the collection fibers causes an illumination zone and a collection zone to overlap at a point external to the window.

* * * * *